(12) United States Patent
Bryant et al.

(10) Patent No.: US 6,288,108 B1
(45) Date of Patent: Sep. 11, 2001

(54) METHODS FOR INCREASING LEVELS OF ACETYLCHOLINE

(75) Inventors: Henry Uhlman Bryant, Indianapolis, IN (US); Michele Annette Glinn, Okemos, MI (US); Steven Marc Paul; Xin Wu, both of Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/700,505

(22) PCT Filed: Jun. 4, 1999

(86) PCT No.: PCT/US99/12603

§ 371 Date: Nov. 14, 2000

§ 102(e) Date: Nov. 14, 2000

(87) PCT Pub. No.: WO99/65309

PCT Pub. Date: Dec. 23, 1999

Related U.S. Application Data

(60) Provisional application No. 60/089,488, filed on Jun. 16, 1998.

(51) Int. Cl.⁷ ............................ A61K 31/38; A01N 43/12
(52) U.S. Cl. ............................................................. 514/443
(58) Field of Search ............................................... 514/443

(56) References Cited

U.S. PATENT DOCUMENTS

| | | | |
|---|---|---|---|
| 4,623,660 | 11/1986 | Richardson | 514/514 |
| 5,389,670 | 2/1995 | Fontana | 514/443 |
| 5,393,763 | 2/1995 | Black et al. | 514/333 |
| 5,462,950 | 10/1995 | Fontana | 514/324 |
| 5,508,292 | 4/1996 | Sall et al. | 514/324 |
| 5,510,357 | 4/1996 | Palkowitz | 514/324 |
| 5,512,296 | 4/1996 | Cullinan | 424/451 |
| 5,534,526 | 7/1996 | Cullinan | 514/324 |
| 5,550,150 | 8/1996 | Fontana | 514/443 |
| 5,552,415 | 9/1996 | May | 514/324 |
| 5,578,613 | 11/1996 | Bryant et al. | 514/324 |
| 5,604,248 | 2/1997 | Bryant et al. | 514/324 |
| 5,686,476 | 11/1997 | May | 514/324 |

(List continued on next page.)

FOREIGN PATENT DOCUMENTS

| | | |
|---|---|---|
| 663 209A2 | 11/1994 | (EP) . |
| 729 956A1 | 2/1996 | (EP) . |
| 792638 | 9/1997 | (EP) . |
| WO 99/65489 | of 0000 | (WO) . |
| WO 95/17095 | 12/1994 | (WO) . |
| WO 97/46527 | 6/1997 | (WO) . |
| WO 98/45287 | 4/1998 | (WO) . |
| WO 99/65309 | 6/1999 | (WO) . |

OTHER PUBLICATIONS

Aguado et al., "Synthesis and evaluation of tacrine–related compounds for the treatment of Alzheimer's disease", Eur. J. Med. Chem. 29, pp. 205–221, 1994.*

Mohs et al., "Oral Physostigmine Treatment of Patients With Alzheimer's Disease", Am. J. Psychiatry, 142:1, Jan. 1985.*

Wu, X., et al, "Raloxifene increases hippocampal choline acetyltransferase activity in ovariectomized rats." *Society For Neuroscience Abstracts*, vol. 24, No. 1–2, p. 732, 1998 (XP002111355).

Nickelsen, T, et al., "Raloxifene hydrochloride, a selective estrogen receptor modulator: safety assessment of effects on cognitive function and mood in postmenopausal women" Psychoneuroendocrinology (1998) 24(1), 115–128, 1999 (XP002111819).

Fuchs–Young, R. et al., "Preclinical demonstration of specific and potent inhibition of mammary tumor growth by new selective estrogen receptor modulators (SERMS)" Proceedings of the *American Association For Cancer Research Annual Meeting* (1997) vol., 38 No. 0, p. 573 (XP002111820).

Mohs, et al. "Oral Physostigmine Treatment of Patients with Alzheimer's Disease" *American Journal of Psychiatry*, vol., 142, 1985 (XP002080514).

Aguado, F. et al., "Synthesis and Evaluation of Tacrine–Related Compounds for the Treatment of Alzheimer's Disease" *European Journal of Medicinal Chemistry Chimica Therapeutica*, vol., 29, 1994 (XP000616050).

Xin Wu, et al, "Brain Research" Raloxifene and estradiol benzoate both fully restore hippocampal choline acetyltransferase activity in ovariectomized rats, 847, 19999.

Kirkland, et al., "Tamoxifene Stimulates Expression of the c–fos Proto–Oncogene in Rodent Uterus", Molecular Pharm vol. 43 709–714, 1993.

(List continued on next page.)

Primary Examiner—Dwayne C. Jones
(74) Attorney, Agent, or Firm—William R. Boudreaux; Gilbert T. Voy

(57) ABSTRACT

The current invention relates to a method for increasing levels of acetylcholine comprising administering to a mammal in need thereof, an effective amount of a compound of formula (I), and optionally an AChE inhibitor.

(I)

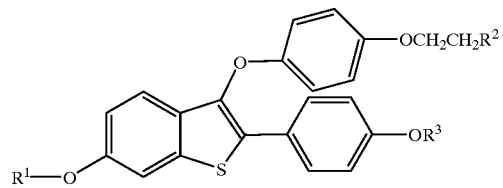

16 Claims, No Drawings

U.S. PATENT DOCUMENTS

| | | | |
|---|---|---|---|
| 5,731,342 | 3/1998 | Cullinan et al. | 514/443 |
| 5,843,934 | 12/1998 | Simpkins | 514/182 |

OTHER PUBLICATIONS

Jordan, et al., "Tamoxifen–stimulated Growth of Human Endometrial Carcinoma" New York Academy of sciences.

Malfetano, "Tamoxifen–Associated Endometrial Carcinoma in Postmenopausal Breast Cancer Patients", Academic Press, 1990.

"Women on Estrogen Appear at Less Risk of Alzheimer's", Indianapolis, Star, Nov. 10, 1993.

* cited by examiner

METHODS FOR INCREASING LEVELS OF ACETYLCHOLINE

This application is a 371 of PCT/US99/12603, filed on Jun. 4, 1999. Which claims benefit of Provisional No. 60/089,488 filed Jun. 16, 1998.

The present invention deals with the disciplines of medicinal chemistry, neurophysiology, and neuropharmacology. Specifically, the present invention is related to increasing levels of acetylcholine by the administration of 2-aryl-3-aryloxybenzo[b]thiophenes.

Cholinergic neurons make up a major neuronal system of the central and peripheral nervous systems. Cholinergic neurons are associated especially with the neurotransmitter acetylcholine. In the central nervous system, acetylcholine is a neurotransmitter and can be found in, among other places, the hippocampus and frontal cortex of the brain.

The hippocampal area of the brain, particularly those areas which are known to involve cholinergic neurons, is believed to have functions associated with cognition, learning, and memory. Degenerative diseases with symptoms such as loss of cognition, learning, and memory, have been linked to a loss in cholinergic neurons. For example, it is known that in patients suffering from Alzheimer's disease, there is a marked decrease in the level of cholinergic neurons in the hippocampus. The progressive loss of these cholinergic neurons appears to mirror the progressive loss in memory and cognitive function in these patients. It is thought that one reason for the decline of these neurons is the loss or decreased function of the neurotransmitter, acetylcholine. Several potential therapies which are designed to increase levels of acetylcholine are being clinically evaluated.

The level of acetylcholine in a neuron is basically determined by where the equilibrium between its biosynthesis and bio-degradation lies. The enzyme choline acetyltransferase (ChAT) is primarily responsible for its synthesis and acetylcholineesterase (AChE) for its degradation. One therapeutic strategy for increasing the level of acetylcholine is based on blocking its degradation via inhibition of AChE, e.g., using AChE inhibitors such as physostigmine salicylate, tacrine hydrochloride, donepezil hydrochloride and the like. Although, there are some encouraging results with the clinical use of AChE inhibitors, especially in early stages of Alzheimer's disease, these agents generally have undesirable side effects, because of their non-specific, systemic action. Currently, tacrine has been approved for the early treatment of Alzheimer's symptoms, (See "Goodman and Gilman's, The Pharmacological Basis of Therapeutics", Ed. Gilman, et al., Pergamon Press, 8$^{th}$ Ed., Chap.7, (1990) and references cited, therein).

Another therapeutic strategy for increasing levels of acetylcholine is based on up-regulating ChAT in the neurons. It has been found that the hormone, estrogen, increases the level of acetylcholine by up-regulating ChAT in the hippocampus of rats (see "Immunochemical demonstration of increased choline acetyltransferase concentration in rat preoptic area after estradiol administration", Luine, et al., Brain Res., 191:273–277, 1980, "Estradiol Increases Choline Acetyltransferase Activity in Specific Basal Forebrain Nuclei and Projection Areas of Female Rats", Luine, V., Exp. Neurology, 89:484–490, 1985, "Ovarian steroid deprivation results in a reversible learning impairment and compromised cholinergic function in female Sprague-Dawley rats", Singh, M., et al., Brain Res., 644:305–312, 1994). It, therefore, has been speculated, and preliminary clinical information confirms, that post-menopausal women treated with hormone replacement therapy (estrogen with or without progestins) may be less likely to succumb to Alzheimer's disease or should have existing symptoms alleviated.

However, therapy with estrogen has undesirable side-effects, including uterotrophic effects, a possible increase in breast cancer incidence, bloating, resumption of menses, etc., which limits patient compliance. Thus, the opportunity exists for new and improved therapeutic interventions to increase levels of acetylcholine.

The current invention relates to a method for up-regulating choline acetyltransferase (ChAT) in mammals comprising administering to a mammal in need thereof an effective amount of a compound of formula I:

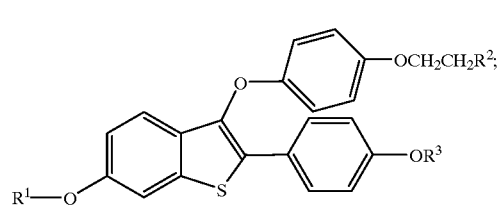

or a pharmaceutical acid addition salt or solvate thereof; where:

$R^1$ and $R^3$ are independently hydrogen, methyl, benzoyl, substituted benzoyl, or C(O)—($C_1$–$C_6$ alkyl);

$R^2$ is selected from the group pyrolidin-1-yl, piperidin-1-yl, and hexamethyleneimin-1-yl; where the $R^2$ group is optionally the N-oxide; and optionally a choline esterase inhibitor.

In addition, the present invention relates to a method for increasing the levels of acetylcholine in the frontal cortex and/or hippocampus regions of the brain in mammals comprising administering to a mammal in need thereof, an effective amount of a compound of formula I, or a pharmaceutical acid addition salt or solvate thereof; and optionally a choline esterase inhibitor.

Further, the present invention relates to a method for inhibiting conditions or detrimental effects caused by a deficiency of choline acetyltransferase and/or acetylcholine in the frontal cortex and/or hippocampus regions of the brain in mammals comprising administering to a mammal in need thereof, an effective amount of a compound of formula I, or a pharmaceutical salt or solvate thereof; and optionally a choline esterase inhibitor.

Moreover, the present invention relates to a pharmaceutical formulation comprising a compound of formula I, or a pharmaceutical acid addition salt or solvate thereof, an acetylcholineesterase (AChE) inhibitor; and a pharmaceutical carrier, diluent, or excipient.

The current invention is related to the discovery that a select group of 2-aryl-3-aryloxybenzo[b]thiophenes, i.e., compounds of formula I, are useful for up-regulating ChAT, and, therefore, are useful for increasing levels of acetylcholine in neurons which contain acetylcholine and ChAT.

A preferred embodiment of all methods of the present invention is where the mammal to be administered a compound of formula I is a human, particularly a female human, and most particularly when that human female is estrogen deficient. However, human males are also contemplated under the term "mammal", particularly males who are testosterone deficient.

Another preferred embodiment of the present invention is where the condition caused by a decrease of choline acetyltransferase and/or acetylcholine in the frontal cortex and/or hippocampus regions of the brain is Alzheimer's disease.

Moreover, another preferred embodiment of all methods of the present invention is the use of a pharmaceutical acid addition salt of a compound of formula I where $R^1$ is hydrogen, $R^3$ is methyl, and $R^2$ is pyrolidin-1-yl. More preferably, the salt is the hydrochloride. This more preferred compound is named 2-(4-methoxyphenyl)-3-(4-[2-(pyrolidin-1-yl) ethoxy]phenoxy-6-hydroxybenzo[b]thiophene hydrochloride.

An even more preferred embodiment of all methods of the present invention is the use of a pharmaceutical acid addition salt of a compound of formula I where $R^1$ is hydrogen, $R^3$ is methyl, and $R^2$ is piperidin-1-yl. Most preferably, the salt is the hydrochloride. This most preferred compound is named 2-(4-hydroxyphenyl)-3-(4-[2-(piperidin-1-yl) ethoxy]phenoxy)-6-hydroxybenzo [b]thiophene hydrochloride.

The present invention contemplates the optional use of currently known AChE inhibitors such as physostigmine salicylate, tacrine hydrochloride, donepezil hydrochloride and the like, as well as agents that are later found to be AChE inhibitors.

As used herein, the term "effective amount" means an amount of a compound of formula I which is capable of up-regulating ChAT and/or increasing levels of acetylcholine in the hippocampus and frontal cortex regions of the brain and/or inhibiting conditions or detrimental effects caused by a decrease of choline acetyltransferase and/or acetyl in mammals. When a compound of formula I is co-administered with an AChE inhibitor the term "effective amount" also means an amount of such an agent capable of inhibiting AChE.

The term "estrogen deprived" refers to a condition, either naturally occurring or clinically induced, where a woman can not produce sufficient estrogenic hormones to maintain estrogen dependent functions, e.g., menses, homeostasis of bone mass, neuronal function, cardiovascular condition, etc. Such estrogen deprived situations arise from, but are not limited to, menopause and surgical or chemical ovarectomy, including its functional equivalent, e.g., medication with GnRH agonists or antagonists, ICI 182780, and the like.

The term "inhibiting" in the context of inhibiting conditions or detrimental effects caused by a deficiency of ChAT and/or acetylcholine in the frontal cortex and/or hippocampus regions of the brain includes its generally accepted meaning, i.e., prohibiting, restraining, alleviating, ameliorating, slowing, stopping, or reversing the progression or severity of a decrease in ChAT and acetylcholine and the pathological sequelae, i.e., symptoms, resulting from that event.

The term "up-regulating ChAT" refers to increasing the enzymatic activity of ChAT, i.e., promoting the conversion of choline to acetylcholine. This promotion would include an increase in the efficiency and/or rate of reaction of ChAT and choline and/or an increase in the amount of ChAT present at the site of action. This increase in the amount of enzyme present may be due to gene regulation or other synthetic step of the enzyme's formation and/or a decrease in the enzyme's de-activation and metabolism.

General terms used in the description of compounds herein described bear their usual meanings. For example, "$C_1$–$C_6$ alkyl" refers to straight, branched, or cyclic aliphatic chains of 1 to 6 carbon atoms including methyl, ethyl, propyl, iso-propyl, cyclopropyl, n-butyl, pentyl, hexyl and the like.

The term "substituted benzoyl" refers to benzoyl group having one to five substituents selected independently from the group $C_1$–$C_4$ alkyl, $C_1$–$C_4$ alkoxy, hydroxy, nitro, chloro, fluoro, or tri(chloro or fluoro)methyl.

The term "pharmaceutical" when used herein as an adjective, means substantially non-toxic and substantially non-deleterious to the recipient.

By "pharmaceutical formulation" it is further meant that the carrier, solvent, excipients and salt must be compatible with the active ingredient of the formulation (a compound of formula I).

The term "acid addition salt" refers to a salt of a compound of formula I prepared by reaction of a compound of formula I with a mineral or organic acid. For exemplification of pharmaceutical acid addition salts see, e.g., Berge, S. M, Bighley, L. D., and Monkhouse, D. C., J. *Pharm. Sci.*, 66:1, 1977.

The term "solvate" represents an aggregate that comprises one or more molecules of the solute, such as a formula I compound, with one or more molecules of a pharmaceutical solvent, such as water, ethanol, and the like.

Compounds of formula I where R and/or $R^3$ are hydrogen or methyl may be prepared according to known procedures, such as those detailed in U.S. Pat. Nos. 5,510,357, 5,723, 474, and 5,731,342, the teachings of each are herein incorporated by reference. The compounds of formula I which are carboxylic esters ($R^1$ and/or $R^3$ are C(O)—($C_1$–$C_6$ alkyl), benzoyl, or substituted benzoyl) may be prepared from compounds of formula I where R and/or $R^3$ are hydrogen essentially by methods described in U.S. Pat. No. 5,393,763, the teachings of which are herein incorporated by reference.

The pharmaceutical acid addition salts of the invention are typically formed by reacting a compound of formula I with an equimolar or excess amount of acid. The reactants are generally combined in a mutual solvent such as diethylether, tetrahydrofuran, methanol, ethanol, isopropanol, benzene, and the like. The salts normally precipitate out of solution within about one hour to about ten days and can be isolated by filtration or other conventional methods.

Acids commonly employed to form acid addition salts are inorganic acids such as hydrochloric acid, hydrobromic acid, iydroiodic acid, sulfuric acid, phosphoric acid, and the like, and organic acids such as p-toluenesulfonic, methanesulfonic acid, ethanesulfonic acid, oxalic acid, p-bromophenylsulfonic acid, carbonic acid, succinic acid, citric acid, tartaric acid, benzoic acid, acetic acid, and the like.

Physostigmine salicylate, tacrine hydrochloride, donepezil hydrochloride and other AChE inhibitors are commercially available.

Pharmaceutical formulations can be prepared by procedures known in the art. For example, a compound of formula I, and optionally an AChE inhibitor, can be formulated with common excipients, diluents, or carriers, and formed into tablets, capsules, and the like. Thus, a compound of formula I and an AChE inhibitor can be formulated and administered together. A compound of formula I and an AChE inhibitor may also be administered separately.

Examples of excipients, diluents, and carriers that are suitable for formulation include the following fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonire; and lubricants such as talc, calcium and magnesium stearate and solid polyethyl glycols. Final pharmaceutical forms may be pills, tablets, powders, lozenges, syrups, aerosols, saches, cachets, elixirs, suspensions, emulsions, ointments, suppositories, sterile injectable solutions, or sterile packaged powders, depending on the type of excipient used.

Additionally, the compounds of formula I are well suited to formulation as sustained release dosage forms. The formulations can also be so constituted that they release the active ingredient only or preferably in a particular part of the intestinal tract, possibly over a period of time. Such formulations would involve coatings, envelopes, or protective matrices which may be made from polymeric substances or waxes.

The particular dosage of a compound of formula I required to up-regulate ChAT, and optionally the dosage of an AChE inhibitor required to inhibit AChE, according to this invention will depend upon the particular circumstances of the conditions to be treated. Considerations such as dosage, route of administration, and frequency of dosing are best decided by the attending physician. Generally, an effective minimum dose for oral or parenteral administration of a compound of formula I is about 1, 5, 10, 15, or 20 mg. Typically, an effective maximum dose is about 800, 100, 60, 50, or 40 mg. Most typically the dose ranges between 5 mg and 60 mg (expressed as the amount of the free base of a compound of formula I). Such dosages will be administered to a patient in need of treatment from one to three times each day or as often as needed to effectively up-regulate ChAT, and/or increase the levels of acetylcholine in the frontal cortex and/or hippocampus regions of the brain and/or inhibit conditions or detrimental effects caused by a deficiency of choline acetyltransferase and/or acetylcholine in the frontal cortex and/or hippocampus regions of the brain.

The formulations which follow are given for purposes of illustration and are not intended to be limiting in any way. The total active ingredients in such formulations comprises from 0.1% to 99.9% by weight of the formulation. The term, "active ingredient" means a compound of formula I, or a pharmaceutical salt or solvate thereof, and optionally an AChE inhibitor. Preferably, the compound of formula I is the hydrochloride salt where $R^1$ is hydrogen, $R^3$ is methyl, and $R^2$ is pyrolidin-1-yl. An even more preferred formulation of a compound of formula I would be the hydrochloride salt where $R^1$ is hydrogen, $R^3$ is methyl, and $R^2$ is piperidin-1-yl.

FORMULATION 1

Gelatin Capsules

| Ingredient | Quantity (mg/capsule) |
| --- | --- |
| Active Ingredient | 50–600 |
| Starch NF | 0–500 |
| Starch flowable powder | 0–500 |
| Silicone fluid 350 centistrokes | 0–15 |

The ingredients are blended, passed through a No. 45 mesh U.S. sieve, and filled into hard gelatin capsules.

FORMULATION 2

Tablets

| Ingredient | Quantity (mg/tablet) |
| --- | --- |
| Active Ingredient | 50–600 |
| Starch | 10–50 |
| Cellulose, microcrystalline | 10–20 |
| Polyvinylpyrrolidone (as 10% solution in water) | 5 |
| Sodium carboxymethyl cellulose | 5 |
| Magnesium stearate | 1 |
| Talc | 1–5 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules thus produced are dried at 50–60° C. and passed through a No. 18 mesh U.S. sieve. The sodium carboxymethyl cellulose, magnesium stearate, and talc, previously passed through a No. 60 mesh U.S. sieve, are added to the above granules and thoroughly mixed. The resultant material is compressed in a tablet forming machine to yield the tablets.

FORMULATION 3

Aerosol

| Ingredient | Weight % |
| --- | --- |
| Active Ingredient | 0.50 |
| Ethanol | 29.50 |
| Propellant 22 (Chlorodifluoromethane) | 70.00 |

The active ingredient is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

FORMULATION 4

Suspension

| Ingredient | Weight/Volume |
| --- | --- |
| Active Ingredient | 100 mg |
| Sodium carboxymethyl cellulose | 50 mg |
| Syrup | 1.25 mL |
| Benzoic acid solution (0.1M) | 0.10 mL |
| Flavor | q.v. |
| Color | q.v. |
| Purified water to total | 5 mL |

Suspensions each containing 100 mg of a compound of formula I per 5 mL dose are prepared as follows the active ingredient is passed through a No. 45 mesh U.S. sieve and mixed with the sodium carboxymethyl cellulose and syrup to form a smooth paste. The benzoic acid solution, flavor, and color diluted in water are added and mixture stirred thoroughly. Additional water is added to bring the entire mixture to the required volume.

The following demonstration of the methods of the present invention are presented for the purposes of illustration and are not intended to limit the scope of this invention in any way.

Forty female Sprague-Dawley rats (weight range of 300 to 325 g, six months old) are obtained from Harlan. The animals are either bilaterally ovariectomized (OVX) or exposed to a Sham surgical procedure, and then shipped after one week. Upon arrival, they are housed in metal hanging cages in groups of 3 or 4 per cage and have ad libitum access to food and water for two weeks. Room temperature is maintained at 22.2°±1.7° C. with a minimum relative humidity of 40%. The photoperiod in the room is 12 hours light and 12 hours dark.

The animals are dosed daily by subcutaneous injection or oral gavage with either compound 1 (2-(4-hydroxyphenyl)-3-(4-[2-(piperidin-1-yl)ethoxy]phenoxy)-6-hydroxybenzo[b]thiophene hydrochloride), at 3 mg/kg/day in a vehicle containing 10% cyclodextrin, estradiol benzoate at 0.03 or 0.3 mg/kg/day, or vehicle control. Animals were treated for 3 or 10 days. There are twenty animals per each dosing regimen. At the appropriate time intervals, the animals are sacrificed and their brains dissected. The particular portions of the brains are homogenized and assayed. Homogenates from the hippocampus and frontal cortex were processed and determination of ChAT activity was made by a radio-labelled assay of the biosynthesis of acetylcholine. This procedure may be found in Schoepp et al., *J. Neural Transmirss.*, 78:183–193, 1989, the teachings of which are incorporated by reference.

As expected, in the OVX animals, ChAT levels were reduced >50% (p<0.001) compared to the sham operated controls. In contrast, the animals which received compound 1 or estradiol benzoate had significantly (p<0.05) increased levels of ChAT versus the OVX controls and an insignificant difference from the sham controls.

Thus, the current invention provides methods for the treatment and prophylaxis of syndromes related to the loss of memory, learning, and cognitive function, often seen in women who are estrogen deprived, especially post-menopausal women. An example of such a syndrome is senile dementia of the Alzheimer's type. Beneficial effects, such as a decrease in memory loss, associated with administration of a compound of this invention become apparent after chronic administration. For example, post-menopausal women suffering from Alzheimer's disease can expect to demonstrate an amelioration of their disease after 2–12 months of administration of 2-(4-hydroxyphenyl)-3-(4-[2-(piperidin-1-yl)ethoxy]phenoxy)-6-hydroxybenzo[b]thiophene hydrochloride.

The methods of the present invention may also be employed in a prophylactic modality. For example, a group of peri- or post-menopausal women may have their cognitive and memory function evaluated by standard tests. Following the establishment of this baseline, the women are administered 2-(4-hydroxyphenyl)-3- (4-[2- (piperidin-1-yl) ethoxy]phenoxy)-6-hydroxybenzo[b]thiophene hydrochloride for a period 1–5 years. At the end of this time, re-evaluation of cognitive and memory functions by the standard tests show a decrease in loss of these functions relative to a matched set of patients who were given placebo for the same length of time.

We claim:
1. A pharmaceutical formulation comprising a compound of formula I:

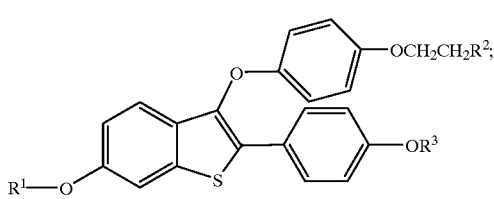

or a pharmaceutical acid addition salt or solvate thereof; where:
   $R^1$ and $R^3$ are independently hydrogen, methyl, benzoyl, substituted benzoyl, or C(O)—($C_1$–$C_6$ alkyl);
   $R^2$ is selected from the group N-pyrolidin-1-yl, piperidin-1-yl, and hexamethyleneimin-1-yl; where the $R^2$ group is optionally the N-oxide; an acetylcholineesterase (AChE) inhibitor; and a pharmaceutical carrier, diluent, or excipient.

2. The formulation according to claim 1 where the acetylcholineesterase (AChE) inhibitor is selected from phys-ostigmine salicylate, tacrine hydrochloride, and donepezil hydrochloride.

3. A method for up-regulating choline acetyltransferase (ChAT) in mammals comprising administering to a mammal in need thereof, an effective amount of a compound of formula I:

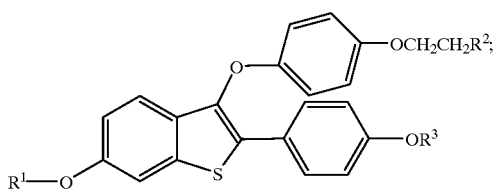

or a pharmaceutical acid addition salt or solvate thereof; where:
   $R^1$ and $R^3$ are independently hydrogen, methyl, benzoyl, substituted benzoyl, or C(O)—($C_1$–$C_6$ alkyl);
   $R^2$ is selected from the group pyrolidin-1-yl, piperidin-1-yl, and hexamethyleneimin-1-yl; where the $R^2$ group is optionally the N-oxide, and optionally an acetyl choline esterase (AChE) inhibitor.

4. A method for increasing the levels of acetyl choline in the frontal cortex and/or hippocampus regions of the brain in mammals comprising administering to a mammal in need thereof, an effective amount of a compound of formula I:

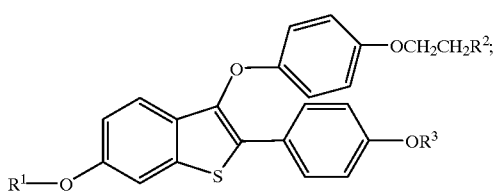

or a pharmaceutical acid addition salt or solvate thereof; where:
   $R^1$ and $R^3$ are independently hydrogen, methyl, benzoyl, substituted benzoyl, or C(O)—($C_1$–$C_6$ alkyl); $R^2$ is selected from the group pyrolidin-1-yl, piperidin-1-yl, and hexamethyleneimin-1-yl; where the $R^2$ group is optionally the N-oxide; and optionally an acetyl choline esterase (AChE) inhibitor.

5. A method for inhibiting conditions or detrimental effects caused by a deficiency of choline acetyltransferase and/or acetyl choline in the frontal cortex and/or hippocampus regions of the brain in mammals comprising administering to a mammal in need thereof, an effective amount of a compound of formula I:

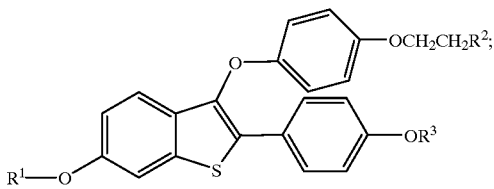

I or a pharmaceutical acid addition salt or solvate thereof; where:

$R^1$ and $R^3$ are independently hydrogen, methyl, benzoyl, substituted benzoyl, or C(O)—($C_1$–$C_6$ alkyl);

$R^2$ is selected from the group N-pyrolidin-1-yl, piperidin-1-yl, and hexamethyleneimin-1-yl; where the $R^2$ group is optionally the N-oxide; and optionally an acetyl choline esterase (AChE) inhibitor.

6. The method according to any of claims 3–5 where the mammal is a female human.

7. The method according to claim 6 where the female human is estrogen deficient.

8. The method according to claim 7 where the compound of formula I is a pharmaceutical acid addition salt, $R^1$ is hydrogen, $R^3$ is methyl, and $R^2$ is piperidin-1-yl.

9. The method according to claim 8 where the compound of formula I is the hydrochloride salt.

10. The method according to claim 7 where the compound of formula I is a pharmaceutical acid addition salt, $R^1$ is hydrogen, $R^3$ is methyl, and $R^2$ is pyrolidin-1-yl.

11. The method according to claim 10 where the compound of formula I is the hydrochloride salt.

12. The method according to claim 5 where the mammal is a human and the condition inhibited is Alzheimer's disease.

13. The method according to claim 12 where the human is an estrogen deficient female.

14. The method according to claim 13 where the compound of formula I is a pharmaceutical acid addition salt, $R^1$ is hydrogen, $R^3$ is methyl, and $R^2$ is piperidin-1-yl.

15. The method according to claim 14 where the compound of formula I is the hydrochloride salt.

16. The method according to either of claims 4 or 5 where the acetyl choline esterase (AChE) inhibitor is selected from physostigmine salicylate, tacrine hydrochloride, and donepezil hydrochloride.

* * * * *